(12) United States Patent
Dakka et al.

(10) Patent No.: US 8,299,281 B2
(45) Date of Patent: *Oct. 30, 2012

(54) PROCESS FOR MAKING TRIGLYCERIDE PLASTICIZER FROM CRUDE GLYCEROL

(75) Inventors: Jihad Mohammed Dakka, Whitehouse Station, NJ (US); Edmund J Mozeleski, Califon, NJ (US); Lisa Saunders Baugh, Ringoes, NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 261 days.

This patent is subject to a terminal disclaimer.

(21) Appl. No.: 12/661,362

(22) Filed: Mar. 16, 2010

(65) Prior Publication Data

US 2010/0249299 A1 Sep. 30, 2010

Related U.S. Application Data

(60) Provisional application No. 61/211,279, filed on Mar. 27, 2009.

(51) Int. Cl.
*C09F 7/02* (2006.01)
*C07C 51/16* (2006.01)
*C07C 51/235* (2006.01)
*C07C 67/48* (2006.01)

(52) U.S. Cl. ............ 554/30; 554/134; 554/227; 560/79; 562/531

(58) Field of Classification Search .................. 554/134, 554/227, 30; 560/79; 562/531
See application file for complete search history.

(56) References Cited

U.S. PATENT DOCUMENTS

| | | | |
|---|---|---|---|
| 3,787,459 A * | 1/1974 | Frankel | 554/120 |
| 3,989,728 A | 11/1976 | Martin | |
| 4,011,251 A | 3/1977 | Tjurin et al. | |
| 4,366,100 A | 12/1982 | Naskar et al. | |
| 4,496,487 A * | 1/1985 | Peerman et al. | 554/213 |
| 5,248,531 A | 9/1993 | Nagai et al. | |
| 6,265,619 B1 | 7/2001 | deRijke | |
| 6,652,774 B2 | 11/2003 | Zhou et al. | |
| 6,734,241 B1 | 5/2004 | Nielsen et al. | |
| 6,740,254 B2 | 5/2004 | Zhou et al. | |
| 6,777,514 B2 | 8/2004 | Patil et al. | |
| 7,087,771 B2 | 8/2006 | Luxem et al. | |
| 7,109,363 B2 | 9/2006 | Brunner et al. | |
| 7,297,738 B2 | 11/2007 | Gosse et al. | |
| 2003/0116750 A1 | 6/2003 | Zhou et al. | |
| 2005/0080279 A1 | 4/2005 | Barbieri et al. | |
| 2005/0215828 A1 | 9/2005 | Garton et al. | |
| 2005/0253109 A1 | 11/2005 | Tran et al. | |
| 2006/0247461 A1 | 11/2006 | Schlosberg et al. | |
| 2008/0025903 A1 | 1/2008 | Cortwright | |
| 2008/0214679 A1 | 9/2008 | Rodriguez-Kabana et al. | |
| 2008/0242895 A1 | 10/2008 | Godwin et al. | |
| 2010/0159177 A1 | 6/2010 | Dakka et al. | |

FOREIGN PATENT DOCUMENTS

| | | |
|---|---|---|
| CN | 1580218 | 2/2005 |
| EP | 719752 | 3/2008 |
| WO | WO 92/22627 | 12/1992 |
| WO | WO 99/32427 | 7/1999 |
| WO | WO 03/029339 | 4/2003 |
| WO | WO 03/050215 | 6/2003 |
| WO | WO 2004/046078 | 6/2004 |
| WO | WO 2007/029724 | 3/2007 |

* cited by examiner

*Primary Examiner* — Tae H Yoon
(74) *Attorney, Agent, or Firm* — Robert A. Migliorini

(57) ABSTRACT

Provided are processes for making, and processes for using triglycerides as plasticizers. Mixed triglyceride plasticizers can be produced by recovery of linear or branched $C_4$ to $C_{13}$ aldehydes from a hydroformylation product, oxidation to the acid with oxygen and/or air, recovery of the resulting acid, and esterification with a crude glycerol, wherein the total carbon number of the triester groups is from 20 to 25 for greater than or equal to 45 wt % of the plasticizer. The product selectivity obtained from esterifying with crude glycerol is comparable to that of esterifying with pure glycerol. Such plasticizers can be phthalate-free and provide outstanding properties including a suitable melting or glass transition or pour point, low volatility, increased compatibility, and excellent low temperature properties in a range of polymeric resins.

21 Claims, 5 Drawing Sheets

PROCESS FOR MAKING TRIGLYCERIDE PLASTICIZER FROM CRUDE GLYCEROL

CROSS-REFERENCE TO RELATED APPLICATION

This application claims priority to U.S. Provisional Application Ser. No. 61/211,279 filed Mar. 27, 2009, herein incorporated by reference in its entirety.

FIELD

The present disclosure relates to a process for making triglycerides based on linear or branched alkyl groups from crude glycerol, useful as plasticizers and viscosity depressants for a wide range of polymer resins.

BACKGROUND

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, poly(vinylidene chloride), nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for about 85% worldwide of PVC plasticizer usage in 2002. However, in the recent past there as been an effort to decrease the use of phthalate esters as plasticizers in PVC, particularly in end uses where the product contacts food, such as bottle cap liners and sealants, medical and food films, or for medical examination gloves, blood bags, and IV delivery systems, flexible tubing, or for toys, and the like. For these and most other uses of plasticized polymer systems, however, a successful substitute for phthalate esters has heretofore not materialized.

One such suggested substitute for phthalates are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, WO 2004/046078, U.S. Application No. 2006-0247461, and U.S. Pat. No. 7,297, 738.

Other suggested substitutes include esters based on benzoic acid (see, for instance, U.S. Pat. No. 6,740,254, and also co-pending, commonly-assigned, U.S. Patent Application 61/040,480 filed Mar. 29, 2008) and polyketones, such as described in U.S. Pat. No. 6,777,514; and also co-pending, commonly-assigned, U.S. application Ser. No. 12/058,397 filed Mar. 28, 2008. Epoxidized soybean oil, which has much longer alkyl groups ($C_{16}$ to $C_{18}$) has been tried as a plasticizer, but is generally used as a PVC stabilizer. Stabilizers are used in much lower concentrations than plasticizers.

Typically, the best that has been achieved with substitution of the phthalate ester with an alternative material is a flexible PVC article having either reduced performance or poorer processability. Thus, heretofore efforts to make phthalate-free plasticizer systems for PVC have not proven to be entirely satisfactory, and this is still an area of intense research.

Plasticizers based on triglycerides have been tried in the past, but they have mostly been based on natural triglycerides from various vegetable oils. The alkyl groups on these natural triglycerides are linear, and can cause compatibility problems when the alkyl chain is too long.

"Structural Expressions of Long-Chain Esters on Their Plasticizing Behavior in Poly(vinyl Chloride)", H. K. Shobha and K. Kishore, Macromolecules 1992, 25, 6765-6769, reported the influence of branching and molecular weight in long-chain esters in PVC. Triglycerides (TGE's) having linear alkyl groups were studied.

"A Method for Determining Compatibility Parameters of Plasticizers for Use in PVC Through Use of Torsional Modulus", G. R. Riser and W. E. Palm, Polymer Engineering and Science, April 1967, 110-114, also investigate the use of triglycerides and their plasticizing behavior with PVC, including tri-iso-valerin (3-methyl butanoate) triglyceride. It was reported that "these materials have volatilities that are much too high for good long-time permanence".

Nagai et al. in U.S. Pat. No. 5,248,531, teaches the use of articles comprising vinyl chloride-type resins (among others) using triglyceride compounds as a hemolysis depressant, and also comprising 10 to 45 wt % of plasticizers selected from trialkyl trimellitates, di-normal alkyl phthalates, and tetraalkyl pyromellitates. The alkyl chains of the acid-derived moiety $R^1$-$R^3$ in the structure below, formula (I), are independently an aliphatic hydrocarbon group of 1 to 20 carbon atoms and in embodiments at least one of the alkyl chains is branched. One specific triglyceride disclosed is glyceryl tri-2-ethylhexanoate.

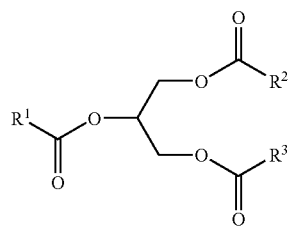

I

Zhou et al. discloses, in U.S. Pat. Nos. 6,652,774; 6,740, 254; and 6,811,722; phthalate-free plasticizers comprising a mixture of different triesters of glycerin, preferably wherein the phthalate-free plasticizer is formed by a process of esterifying glycerin with a mixture comprising a mixture of alkyl acids and aryl acids. Zhou et al. also discloses that glyceryl tribenzoate and glyceryl tri(2-ethyl)hexanoate have not been used as primary plasticizers in vinyl polymers, such as PVC because they are known to be incompatible with such resins.

Nielsen et al., in U.S. Pat. No. 6,734,241, teach a composition comprising a thermoplastic polymer as in formula (I) above, wherein at least one of the R groups is an alkyl group having from 1-5 carbon atoms and at least one of the R groups is a saturated branched alkyl group having from 9 to 19 carbon atoms and a hydrophilic group.

Among the problems presented by the aforementioned triglycerides is they cannot be made conveniently and thus generally are quite expensive and/or are specialty chemicals not suitable as replacements for phthalates from an economic standpoint and/or are not as compatible with the range of polymer systems that phthalates are compatible with, and thus are not viable replacements for phthalates from a physical property standpoint.

For instance, some synthesis methods involve at least two separate steps, such as where the glycerol is first partially esterified with the $C_{10}$ to $C_{20}$ branched chain acyl group and then reacted with acetic acid or acetic anhydride.

Other syntheses involving mixed acid feeds will require addition of a hydrocarbon solvent for azeotropic distillation of the water to drive the esterification reaction to completion (as measured by the hydroxyl number of the ester, which is a measure of the amount of unreacted OH groups), due to the spread in boiling points between the mixed acids. In addition, the use of mixed acid feedstock such as cited in Zhou et al. and in Nielsen et al. can reduce the capability of recycling unreacted acids.

Triglycerides based on acids derived from natural products will be limited to naturally occurring linear alkyl groups with even carbon numbers, which offer very little flexibility in designing an appropriate plasticizer system for a given polymer system.

Thus what is needed is a method of making a general purpose non-phthalate plasticizer having high throughput and providing a plasticizer having a suitable melting or glass transition or pour point, increased compatibility, good performance and low temperature properties.

The production of triglycerides by the esterification of glycerol with a combination of acids derived from the hydroformylation and subsequent oxidation of $C_3$ to $C_{12}$ olefins provides for triglycerides having excellent compatibility with a wide variety of resins. Such triglycerides can be made with a high throughput. For example, esterification of glycerol using a combination of acids eliminates many of the aforementioned problems, and enables high yields of glycerol triesters to be obtained that show excellent compatibility with vinyl polymers. However, it is generally recognized in the art that pure glycerol is needed to yield good triglyceride product selectivity and plasticizer performance, due to the deleterious impact of impurities in the glycerol. Purifying glycerol requires additional manufacturing steps, and hence costs.

Hence, there is a need for a process for producing triglycerides with the use of crude glycerol that yields the comparable triglyceride product selectivity and plasticizer performance to those attainable with pure glycerol.

SUMMARY

The present disclosure is directed to a process for producing a plasticizer including: (i) recovering at least one linear $C_4$ to $C_{13}$ aldehyde, one branched $C_4$ to $C_{13}$ aldehyde, or a combination thereof from a hydroformylation product; (ii) oxidizing the linear, branched or combination thereof $C_4$ to $C_{13}$ aldehyde to form a linear, branched or combination thereof $C_4$ to $C_{13}$ acid; (iii) esterifying the linear, branched or combination thereof $C_4$ to $C_{13}$ acid with a crude glycerol to yield a linear alkyl triglyceride, a branched alkyl triglyceride, or a combination thereof; (iv) purifying the linear, branched or combination thereof alkyl triglyceride to form a plasticizer, wherein the total carbon number of the triester groups (not including the 3 glycerol backbone carbons) ranges from 20 to 25 for greater than or equal to 45 wt % of the plasticizer.

The present disclosure is also directed to a process for producing a plasticizer including: (i) recovering an aldehyde/alcohol mixture including at least one linear $C_4$ to $C_{13}$ aldehyde, one branched $C_4$ to $C_{13}$ aldehyde, or a combination thereof and at least one linear $C_4$ to $C_{13}$ alcohol, one branched $C_4$ to $C_{13}$ alcohol, or a combination thereof from a hydroformylation process; (ii) oxidizing the aldehyde/alcohol mixture to form a linear, branched or combination thereof $C_4$ to $C_{13}$ acid; (iii) esterifying the linear, branched or combination thereof $C_4$ to $C_{13}$ acid with a crude glycerol to yield a linear alkyl triglyceride, a branched alkyl triglyceride, or a combination thereof; (iv) removing the unreacted acid by distillation followed by filtering the esterification product to remove salts and/or ash the followed washing the esterification product with water and/or aqueous carbonate solution to remove salt residuals; and (v) purifying the linear, branched or combination thereof alkyl triglyceride to form a plasticizer, wherein the total carbon number of the triester groups (not including the 3 glycerol backbone carbons) ranges from 20 to 25 for greater than or equal to 45 wt % of the plasticizer.

The present disclosure is still further directed to resin compositions, plastisols and articles produced from the above processes to provide phthalate-free plasticizers, resin compositions, plastisols and articles.

These and other objects, features, and advantages will become apparent as reference is made to the following detailed description, embodiments, examples, and appended claims.

BRIEF DESCRIPTION OF THE DRAWINGS

In the accompanying drawings, like reference numerals are used to denote like parts throughout the several views.

DETAILED DESCRIPTION

Figure 1:
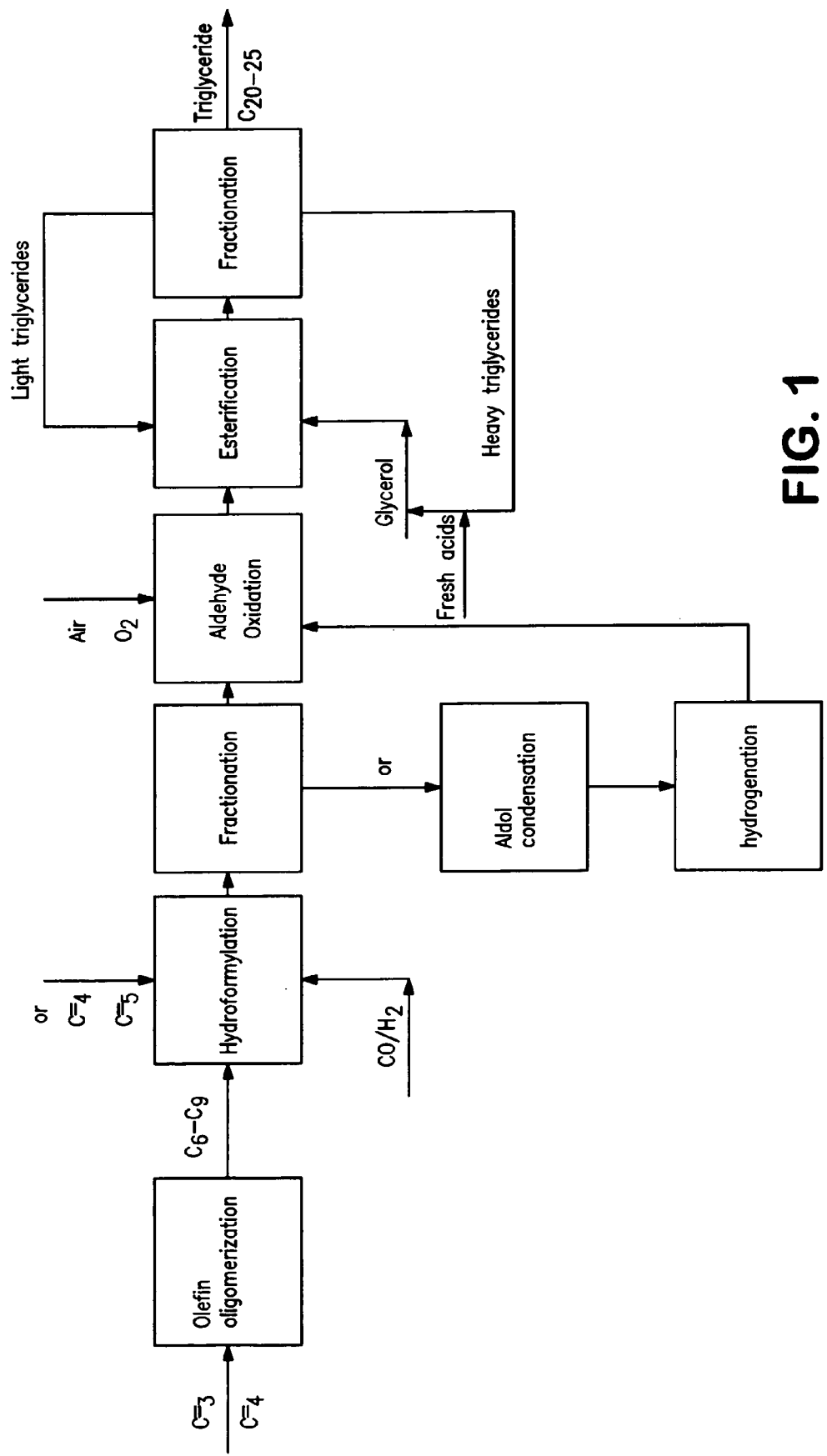
FIG. 1 is a schematic representation of a process according to a preferred embodiment of the invention.

The present disclosure provides methods of making mixed triglycerides using crude glycerol for use as plasticizers for polymer resins.

U.S. Provisional Application No. 61/203,626 filed on Dec. 24, 2008, herein incorporated by reference in its entirety, discloses mixed triglyceride compositions, processes for making, and processes for using triglycerides as plasticizers. In one form of the process for making such mixed triglycerides, the steps include (i) recovering at least one linear $C_4$ to $C_{13}$ aldehyde, one branched $C_4$ to $C_{13}$ aldehyde, or a combination thereof from a hydroformylation product; (ii) oxidizing the linear, branched or combination thereof $C_4$ to $C_{13}$ aldehyde to form a linear, branched or combination thereof $C_4$ to $C_{13}$ acid; (iii) esterifying the linear, branched or combination thereof $C_4$ to $C_{13}$ acid with a polyol to yield a linear alkyl triglyceride, a branched alkyl triglyceride, or a combination thereof; and (iv) purifying the linear, branched or combination thereof alkyl triglyceride to form a plasticizer, wherein the total carbon number of the triester groups ranges from 20 to 25 for greater than or equal to 45 wt % of the plasticizer.

Pure glycerol is one of polyols that may be used in esterifying the linear, branched or combination thereof $C_4$ to $C_{13}$ acid to yield a linear alkyl triglyceride, a branched alkyl triglyceride, or a combination thereof.

With regard to the present disclosure, the applicants have surprisingly discovered that crude glycerol may be used in place of pure glycerol in the esterification process, and still yield a process for making triglycerides with similar properties and performance, including mixed triglycerides with comparable isomer selectivity. One or more benefits of using crude glycerol in place of pure glycerol include, but are not limited to, a lower cost input material for producing triglyceride plasticizers, lower manufacturing cost, and greater manufacturing process simplification.

As used in the instant specification and in the appended claims, the term "crude glycerol" means a glycerol component including not more than 90 wt % of glycerol. Other components may include, but are not limited to, methanol, water, fatty acid, MONG (Matter Organic Not Glycerol), NaCl, ash and/or other impurities. In other forms, the crude glycerol may include not more than 95 wt %, or 88 wt %, or 86 wt %, or 84 wt %, or 82 wt %, or 50 wt % glycerol. In one form of the present disclosure, the triglyceride plasticizer produced from crude glycerol by the disclosed processes is "phthalate-free". As used in the instant specification and in the appended claims, the term "phthalate-free" means that the plasticizer does not contain any phthalate diesters, which are also known in the art simply as phthalates.

Referring to the triglyceride chemical formula below, for the instant application including the claims, the total carbon number of the triester groups is defined as the sum of the carbons for the $R^1$, $R^2$ and $R^3$ groups plus the 3 carbons for the three carbonyl groups, and not including the 3 glycerol backbone carbons. Hence for illustrative purposes, for a $C_8$ triglyceride (also referred to as 8,8,8 triglyceride), the total carbon number would be 24 as defined herein (7+7+7=21 carbons from the $R^1$, $R^2$, and $R^3$ alkyl groups plus three carbonyl group carbons) because the 3 glycerol backbone carbons are not included in the calculation. For a $C_7$ triglyceride (also referred to as 7,7,7 triglyceride), the total carbon number would be 21 as defined herein (6+6+6=18 carbons from the $R^1$, $R^2$, and $R^3$ alkyl groups plus three carbonyl group carbons) because the 3 glycerol backbone carbons again are not included in the calculation.

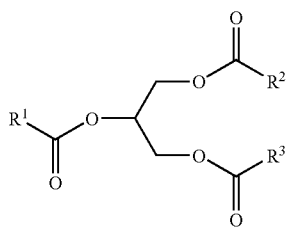

According to the present disclosure, the triglycerides disclosed herein may be produced by esterification of one or more $C_4$ to $C_{13}$ linear or branched acids with crude glycerol to form a triglyceride with a total carbon number of the linear or branched alkyl triester groups ranging from 20 to 25 (including the 3 carbons for the three carbonyl groups and not including the 3 glycerol backbone carbons).

In one embodiment, at least one or more $C_4$ to $C_{13}$ linear or branched acids will be derived from the hydroformylation of light olefins, aldol condensation of the light aldehydes and then hydrogenation followed by oxidation and thus may be referred to herein as "oxo acids". The OXO Process is per se well known. By way of recent examples, see, for instance, U.S. Pat. Nos. 7,345,212; 7,186,874; 7,148,388; 7,081,554; 7,081,553; 6,982,295; 6,969,736; 6,969,735; 6,013,851; 5,877,358; and PCT publications WO2007106215; WO2007040812; WO2006086067; WO2006055106; WO2003050070; WO2000015190. As mentioned above, or alternatively directly oxidized to the desired acid(s). However, it will be recognized by one of skilled in the art that the $C_4$ to $C_{10}$ linear or branched acids may be derived from other processes.

The present disclosure is also directed to the product of the process, which comprises at least one compound according to the following structure (I):

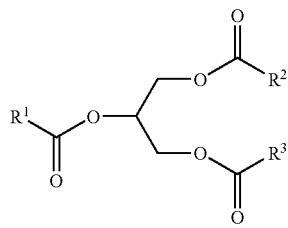

wherein the sum of the carbons for the linear or branched alkyl triester groups ($R^1$, $R^2$, and $R^3$ plus 3 carbons for the three carbonyl groups and not including the 3 glycerol backbone carbons) may range from 20 to 25. Alternatively, the sum of the carbons for the linear or branched alkyl triester groups ($R^1$, $R^2$, and $R^3$ plus 3 carbons for the three carbonyl groups and not including the 3 glycerol backbone carbons) may range from 20 to 24, or 20 to 23, or 20 to 22, or 20 to 21, or 22 to 25, or 23 to 25, or 24 to 25. In another form, the sum of the carbons for the $R^1$, $R^2$, and $R^3$ plus 3 carbons for the three carbonyl groups and not including the 3 glycerol backbone carbons may be 20, or 21, or 22, or 23, or 24, or 25.

The present disclosure is also directed to the product of the process, which comprises at least one compound according to structure (I), wherein the sum of the carbons for the branched alkyl triester groups ($R^1$, $R^2$, and $R^3$ plus three carbons for the three carbonyl groups and not including the three glycerol backbone carbons) may range from 20 to 25, and also wherein $R^1$, $R^2$, and $R^3$ are independently selected from $C_3$ to $C_{12}$ alkyl groups having an average branching of from about 0.8 to 3.0 branches per group or from about 0.8 to about 2.2 branches per group. Average branching is determined by Nuclear Magnetic Resonance (NMR) spectroscopy. In another form of this embodiment, the average branching may range from about 0.8 to about 1.8 branches per group. In yet another form, the average branching of the $C_3$ to $C_{12}$ branched alkyl groups ranges from about 0.8 to about 3.0, or from about 0.8 to about 1.6, or from about 1.2 to about 1.4 branches per group. The average branching of the sidechain groups will be a function of the average branching of the precursor OXO acids used in the esterification process. The average branching per triglyceride of structure (I) will equal three times the average branching per group, since each triglyceride bears three alkyl groups.

In the specific case of $C_7$ triglycerides (also referred to as 7,7,7 triglyceride) wherein the sum of the carbons for the branched alkyl triester groups ($R^1$, $R^2$, and $R^3$ plus 3 carbons for the three carbonyl groups and not including the 3 glycerol backbone carbons) is 21, the process of the present disclosure provides, in one embodiment, an average branching of about 1.2±0.1 branches per group, based on the branching in molecules having branched $C_6$ alkyl chains in each of $R^1$, $R^2$ and $R^3$. In the specific case of $C_8$ triglycerides (also referred to as 8,8,8 triglyceride) wherein the sum of the carbons for the branched alkyl triester groups ($R^1$, $R^2$, and $R^3$ plus 3 carbons for the three carbonyl groups and not including the 3 glycerol backbone carbons) is 24, the process of the present disclosure provides, in other embodiments, an average branching of about 3.0±0.1 branches per group, based on the branching in molecules having branched $C_7$ alkyl chains in each of $R^1$, $R^2$ and $R^3$. In a yet another embodiment, there is a blend of triglycerides having a mixture of $C_3$ to $C_{12}$ branched alkyl chains for each of $R^1$, $R^2$ and $R^3$ resulting in an average branching of about 1.6±0.2, and preferably 1.6±0.1 branches per group.

NMR analyses of the branching found in the OXO acids finds that these branches are typically methyl groups. For example, with the branched $C_7$ OXO acid, typical isomers include 3-methylhexanoic acid, 4-methylhexanoic acid, 5-methylhexanoic acid, as well as some 3,4-dimethylpentanoic acid, 2,4-dimethylpentanoic acid and 2,3-dimethylpentanoic acid. Some n-heptanoic acid is also present. Similar products are found with mixtures of isomers in the $C_8$ and $C_9$ OXO acids. $C_9$ OXO acids when prepared from the OXO reaction using diisobutylene as the olefin feed will give mostly trimethyl branched acids, such a 3,5,5-trimethylhexanoic acid. The OXO acids generally provide more than one isomer.

In the first step of the process for producing triglycerides disclosed herein, linear or branched aldehydes may be produced by hydroformylation of $C_3$ to $C_{12}$ olefins that in turn have been produced by propylene, butene, and/or pentene oligomerization over solid phosphoric acid or zeolite catalysts. The oligomerization processes are per se well-known. See, for instance, U.S. Pat. Nos. 7,253,330, and 7,145,049. The hydroformylation process step is depicted in FIG. 1. The hydroformylation process produces a mixture of aldehydes and alcohols depending upon the catalyst used and the processing conditions. In one form, the hydroformylation reaction may be catalyzed by a metal selected from Groups 8-10 according to the new notation for the Periodic Table as set forth in Chemical Engineering News, 63(5), 27 (1985). In particular, Ru catalysts tend to be more selective toward forming aldehydes as opposed to alcohols compared to Co catalysts. The non-limiting exemplary metal catalysts selected from Rh and Co may also be used with an organic ligand to further improve catalyst activity and selectivity. In another form, the feed for the hydroformylation process may be formed by dimerizing a feedstock selected from propylene, butenes, pentenes and mixtures thereof by solid phosphoric acid or a zeolite dimerization.

In one form, the resulting $C_4$ to $C_{13}$ aldehydes can then be recovered from the crude hydroformylation product stream by fractionation as depicted in FIG. 1 to remove unreacted olefins and the corresponding alcohols. These $C_4$ to $C_{13}$ aldehydes can then in turn be oxidized to their respective $C_4$ to $C_{13}$ acids using air or enriched air as an oxygen source as depicted in FIG. 1. In an alternative form, that avoids the previous fractionation step, the one or more $C_4$ to $C_{13}$ linear or branched alkyl aldehydes/alcohols can be oxidized to the corresponding acids and alcohols and then the unreacted aldehydes purified by distillation. The separated unreacted aldehydes plus the alcohols are oxidized to their corresponding acids. This alternative form may be particularly suitable when using a Ru catalyst during the hydroformylation process. In either of the preceding forms, the distilled aldehydes may be oxidized to an acid followed by fractionation to remove unreacted alcohol. The oxidizing steps may be either catalyzed or non-catalyzed.

Non-limiting exemplary acids include acetic acid, bromoacetic acid, propanoic acid, 2-chloropropanoic acid, 3-chloropropanoic acid, 2-methylpropanoic acid, 2-ethylpropanoic acid, 2-methylbutanoic acid, 3-methylbutanoic acid, 2-ethylbutanoic acid, 2,2-dimethylbutanoic acid, 2,3-dimethylbutanoic acid, 3,3-dimethylbutanoic acid, 2-methylpentanoic acid, 3-methylpentanoic acid, 4-methylpentanoic acid, cyclopentyl acetic acid, cyclopentyl propanoic acid, cyclopentyl hexanoic acid, cyclohexane carboxylic acid, cyclohexane acetic acid, 2-ethylhexanoic acid, nonadecafluorodecanoic acid, decanoic acid, and undecanoic acid.

Following the oxidation reaction, the $C_4$ to $C_{13}$ acids can then be purified by fractionation to remove unreacted aldehydes, lights and heavies formed during oxidation.

The $C_4$ to $C_{13}$ acids can then be esterified as depicted in FIG. 1 with crude glycerol. Crude glycerol is currently an attractive polyol for use to make plasticizers because it is abundantly available. It is, for instance, a major byproduct of biodiesel production. The esterification step using crude glycerol may be catalyzed by at least one metal selected from Ti, Zr or Sn, or a mixture thereof, or catalyzed by an organic acid. In an alternative form, the esterification step using crude glycerol may be uncatalyzed.

As described above, the crude glycerol used to make the mixed triglycerides disclosed herein includes not more than 95 wt %, or 90 wt %, or 88 wt %, or 86 wt %, or 84 wt %, or 82 wt %, or 50 wt % of glycerol. The components that make-up the remainder of the crude glycerol, may include, but are not limited to, methanol, water, fatty acid, MONG, NaCl, ash and/or other impurities. The inorganic impurities are precipitated at the end of the esterification, and are removed by filtration and washing the ester with water. In other words, the esterification reaction is a means of purifying the crude glycerol. Non-limiting exemplary crude glycerols include REG, EIS-739, EIS-740, EIS-733, EIS-724, EIS 56-81-5, IRE and mixtures thereof. The esterification process used to produce mixed triglycerides with the crude glycerols disclosed herein results in mixed triglycerides with productivity selectivities comparable to that of pure glycerol.

In another form of the present disclosure, a mixture of crude glycerol with another polyol may be utilized to produce mixtures of triglycerides and other polyol esters that may be used as plasticizers. Other polyols that may be utilized with crude glycerol during the esterification process include, but are not limited to, ethylene glycol and propylene glycol. Mixtures of crude glycerol with ethylene glycol and/or propylene glycol may include at least 20 wt %, or least 40 wt %, or least 60 wt %, or least 80 wt % crude glycerol with the remainder constituting the other polyol (for example ethylene glycol or propylene glycol). It is preferred that the polyols as part of the crude glycerol or mixtures of crude glycerol with other polyols be fully esterified so that there are a low to negligible amount of free hydroxyl groups. Thus, for example, it is preferred that the glycerol component of the crude glycerol is esterified to the triester.

Single carbon number linear or branched acids can be used in the esterification, or linear or branched acids of differing carbon numbers can be used to optimize product cost and performance requirements. Hence, a combination of one or more linear or branched $C_4$ to $C_{13}$ acids may be esterifed to form mixed triglycerides including linear or branched alkyl esters, wherein the total carbons for the triester groups ($R^1$, $R^2$, and $R^3$ plus 3 carbons for the three carbonyl groups and not including the 3 glycerol backbone carbons) ranges from 20 to 25. Such range of total carbons for the triester groups yields triglycerides with outstanding performance when used as plasticizers for polymeric resins. More particularly, triglycerides with linear or branched alkyl groups and a total carbon number of the triester groups ranging from 20 to 25 have been discovered to yield low volatility and excellent compatibility with a broad range of polymeric resins, including PVC. Such triglycerides also yield outstanding low temperature performance properties.

Following the esterification process, a fractionation process, such as distillation, may be used to separate the $C_{20}$ to $C_{25}$ triglycerides from the lighter and heavier triglycerides. The light triglycerides may be recycled back to the esterification step of the process. The heavy triglycerides may also be recycled back to the esterification step of the process after adding fresh acids and polyol. The $C_{20}$ to $C_{25}$ triglyceride may be chosen from triglyceride 6,6,9, triglyceride 6,9,6, triglyceride 6,9,9, triglyceride 9,6,9, triglyceride 5,5,10, triglyceride 5,10,5, triglyceride 5,10,10, triglyceride 10,5,10, triglyceride 6,7,7, triglyceride 7,6,7, and triglyceride 7,7,7. Note however that these $C_{20}$ to $C_{25}$ triglycerides may include other proportions (55 wt % or less relative to the total) of triglycerides which do not have a total carbon number of the triester groups falling within the 20 to 25 range. If the total weight % of these non-inventive triglycerides is greater than 55 wt %, plasticizer properties (volatility, compatibility, low temperature performance, etc.) will begin to be negatively impacted. Hence, for the $C_{20}$ to $C_{25}$ triglycerides disclosed herein, linear or branched alkyl triglycerides with a total carbon number of from 20 to 25 should comprise greater than or equal to 45 wt %, or greater than or equal to 60 wt %, or greater than or equal to 75 wt %, or greater than or equal to 90 wt %, or greater than or equal to 95 wt %, or greater than or equal to 97 wt %, or greater than or equal to 99 wt %, or greater than or equal to 99.5 wt %, or greater than or equal to 99.9 wt % of the plasticizer. The fractionation process following the esterification step may be used to increase the purity of $C_{20}$ to $C_{25}$ triglycerides.

The chemistry and a simplified process to produce triglycerides via the route described above is shown in equations (1)-(3), below. For equation (3), the glycerol is based on a crude glycerol feed stream. For simplicity, the branched hexene feed example is shown in eqn (1), but the feed can be linear or branched butene, pentenes, hexenes, heptenes, octenes or nonenes as the starting olefins. As discussed above, the resulting $C_4$, $C_5$, $C_6$, $C_7$, $C_8$, $C_9$, $C_{10}$ and $C_{13}$ acids may be used individually or together in mixtures to make mixed carbon number esters to be used as plasticizers as long as the sum of carbons for the triester groups ($R^1$, $R^2$, and $R^3$ plus 3 carbons for the three carbonyl groups and not including the 3 glycerol backbone carbons) for greater than or equal to 45 wt % of the plasticizer product is from 20 to 25. Correspondingly, the $C_4$-$C_{13}$ acids may be linear, branched, or a combination thereof. This mixing of carbon numbers and levels of branching may be manipulated to achieve the desired compatibility with PVC for the respective polyol used for the polar end of the plasticizer, and to meet other plasticizer performance properties.

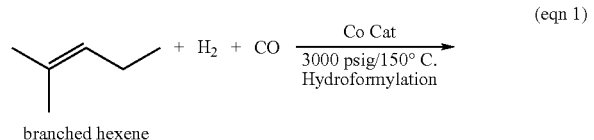

(eqn 1)

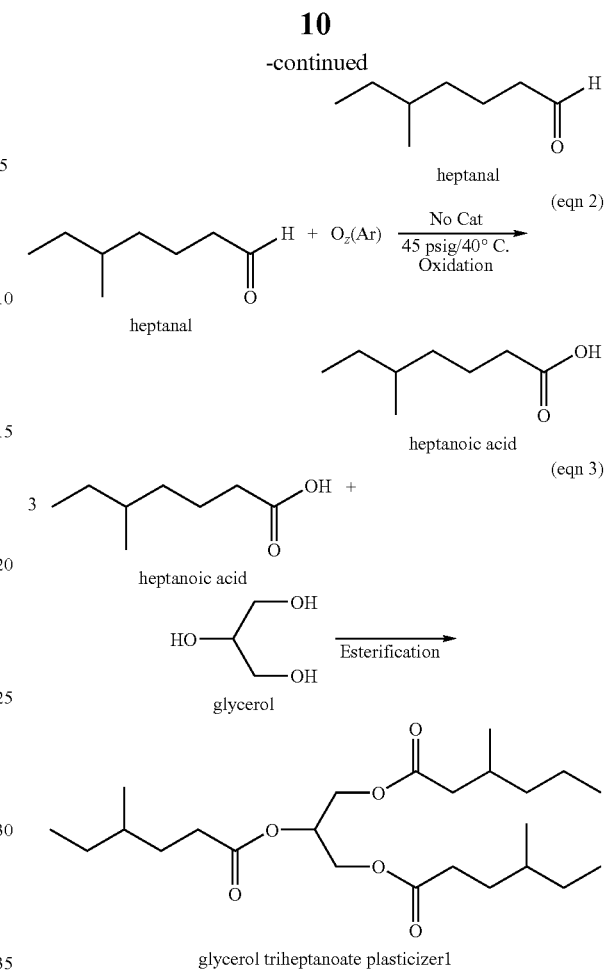

Equations 4-7 (designated 4-, 5-, 6- and 7-below) are as follows:

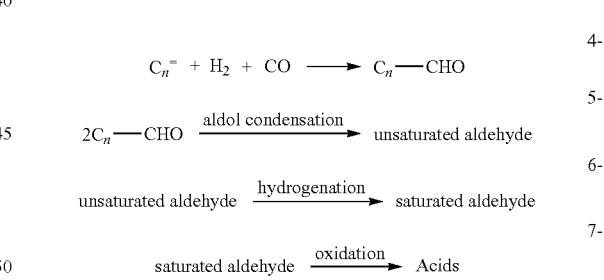

The applicability of the triglyceride structures as potential PVC plasticizers can be screened by estimating their relative solubility in PVC using Small's group contribution method to calculate solubility parameters for each structure (see The Technology of Plasticizers by J. Sears and J. Darbey, John Wiley & Sons, New York, 1982, pp 95-99, discussing using the Small formula to looking at plasticizer compatibility with PVC; this paper sites as a reference, the original work by Small: Small, P. A., "Some Factors Affecting the Solubility of Polymers", J. Appl. Chem, 3, pp 76-80 (1953); see also using Small's group contribution values from the Polymer Handbook, 3rd Ed., J. Brandrup & E. H. Immergut, Eds. John Wiley, New York, (1989)). These calculations are shown below in Table 1 for the $C_6$ triglyceride (also referred to as 6,6,6 triglyceride):

TABLE 1

$C_6$ Triglyceride

|  | Solubility | Number | Solubility Contrib | MW | MW Contrib |
|---|---|---|---|---|---|
| $CH_3$ | 214 | 6 | 1284 | 15 | 90 |
| —$CH_2$— | 133 | 8 | 1064 | 14 | 112 |
| —CH= | 28 | 4 | 112 | 13 | 52 |
| COO esters | 310 | 3 | 930 | 44 | 132 |
|  |  |  | 3390 |  | 386 |
| Solubility Parameter = |  |  | 8.43 | Density = | 0.96 |
| Delta to PVC = |  |  | −1.23 |  |  |

However, the solubility parameter data alone does not predict both compatibility and volatility in PVC. The $C_6$ triglyceride (also referred to as 6,6,6 triglyceride) composition with a total carbon number of 18 (excluding the 3 glycerol backbone carbons) yields excessive volatility when used in PVC resins as a plasticizer, although compatibility is adequate.

Likewise, the solubility may also be calculated for the $C_7$ triglyceride (also referred to as 7,7,7 triglyceride), as shown in Table 2:

TABLE 2

$C_7$ Triglyceride

|  | Solubility | Number | Solubility Contrib | MW | MW Contrib |
|---|---|---|---|---|---|
| $CH_3$ | 214 | 6 | 1284 | 15 | 90 |
| —$CH_2$— | 133 | 11 | 1463 | 14 | 154 |
| —CH= | 28 | 4 | 112 | 13 | 52 |
| COO esters | 310 | 3 | 930 | 44 | 132 |
|  |  |  | 3789 |  | 428 |
| Solubility Parameter = |  |  | 8.50 | Density = | 0.96 |
| Delta to PVC = |  |  | −1.16 |  |  |

The $C_7$ triglyceride (also referred to as 7,7,7 triglyceride) composition with a total carbon number of 21 (excluding the 3 glycerol backbone carbons) yields adequate volatility and excellent compatibility when used in PVC resins as a plasticizer.

Table 3 shows the solubility values calculated by the same method for the $C_8$ triglyceride (also referred to as 8,8,8 triglyceride):

TABLE 3

$C_8$ Triglyceride

|  | Solubility | Number | Solubility Contrib | MW | MW Contrib |
|---|---|---|---|---|---|
| $CH_3$ | 214 | 6 | 1284 | 15 | 90 |
| —$CH_2$— | 133 | 14 | 1862 | 14 | 196 |
| —CH= | 28 | 4 | 112 | 13 | 52 |
| COO esters | 310 | 3 | 930 | 44 | 132 |
|  |  |  | 4188 |  | 470 |
| Solubility Parameter = |  |  | 8.55 | Density = | 0.96 |
| Delta to PVC = |  |  | −1.11 |  |  |

The $C_8$ triglyceride (also referred to as 8,8,8 triglyceride) composition with a total carbon number of 24 (excluding the 3 glycerol backbone carbons) yields adequate volatility and excellent compatibility when used in PVC resins as a plasticizer.

Table 4 shows the solubility values calculated by the same method for the $C_9$ triglyceride (also referred to as 9,9,9 triglyceride):

TABLE 4

$C_9$ Triglyceride

|  | Solubility | Number | Solubility Contrib | MW | MW Contrib |
|---|---|---|---|---|---|
| $CH_3$ | 214 | 6 | 1284 | 15 | 90 |
| —$CH_2$— | 133 | 17 | 2261 | 14 | 238 |
| —CH= | 28 | 4 | 112 | 13 | 52 |
| COO esters | 310 | 3 | 930 | 44 | 132 |
|  |  |  | 4587 |  | 512 |
| Solubility Parameter = |  |  | 8.6 | Density = | 0.96 |
| Delta to PVC = |  |  | −1.06 |  |  |

Again, however, the solubility parameter data alone does not predict both excellent compatibility and volatility in PVC. The $C_9$ triglyceride (also referred to as 9,9,9 triglyceride) composition with a total carbon number of 27 (excluding the 3 glycerol backbone carbons) yields adequate volatility, but inferior compatibility when used in PVC resins as a plasticizer.

The solubility parameter of PVC is calculated by the same Small's Group Contribution Method to be 9.66. The differences in solubility parameters between the triglyceride structures in FIG. 1 and PVC are shown in Tables 1-4. These differences from PVC range from 1.23 for the $C_6$ triglyceride (also referred to as 6,6,6 triglyceride) to 1.06 units for the $C_9$ triglyceride (also referred to as 9,9,9 triglyceride), which indicates reasonable expected solubility in PVC for these materials. As references, the solubility parameters for two well-known phthalate plasticizers, di-isononyl phthalate (DINP) and di-isodecyl phthalate (DIDP) are 8.88 (delta to PVC=0.78), and 8.56 (delta to PVC=1.10) respectively. The estimated solubility parameter for one non-phthalate plasticizer, di-isononyl cyclohexanoate, is 7.32 by Small's method. This is a difference of 2.34 solubility parameter units from PVC.

A non-limiting process embodiment is illustrated in FIG. 1. Propylene is used as feedstock to an oligomerization reaction. The reaction may be continuous, batch, or semibatch. Unreacted $C_3$ olefins are distilled off and optionally recycled. Trimers and tetramers may be recovered as bottoms product with the desired dimer hexene taken as a sidestream and send to the hydroformylation reaction. Carbon monoxide and hydrogen, conveniently supplied as Syngas, are also supplied to the reactor. The products are then separated by fractionation, with light olefins optionally recycled and the $C_7$ aldehydes and $C_7$ alcohols being separated. The amount of aldehyde and alcohols produced may be attenuated in the hydrofinishing section. In an embodiment, the $C_7$ aldehydes are then oxidized with the addition of air and/or oxygen, and unreacted aldehydes and heavies are separated out. The desired product $C_7$ acid is then esterified with crude glycerol and recovered as the triglyceride with a total carbon number (excluding the 3 glycerol backbone carbons) of the triester groups of 21.

In another form of the present disclosure, a composition comprising a blend of two or more different triglycerides may also provide outstanding plasticizer performance in range of polymer resins, including PVC. The blend of the two or more different triglycerides should include triglycerides according to the composition and process of making disclosed herein. That is, each triglyceride in the mixed triglyceride blend includes a linear or branched alkyl triglyceride; wherein the total carbon number of the triester groups ranges from 20 to 25. In one form, the mixed triglyceride includes a two component blend of triglyceride 6,6,9/6,9,6 and 6,9,9/9,6,9. In another form, the mixed triglyceride includes a two component blend of triglyceride 5,5,10/5,10,5 and 5,10,10/10,5,10. In yet another form, the mixed triglyceride includes a two component blend of triglyceride 6,7,7/7,6,7 and triglyceride 7,7,7. Note however that these mixed triglyceride blends may include other proportions (defined herein as 55 wt % or less relative to the total) of triglycerides which do not have a total carbon number of the triester groups falling within the 20 to 25 range. If the total weight % of these non-inventive triglycerides is greater than 55 wt % in the mixed triglyceride blend, plasticizer properties (volatility, compatibility, low temperature performance, etc.) will begin to be negatively impacted. Hence, for the mixed triglycerides disclosed herein, linear or branched alkyl triglycerides with a total carbon number (excluding the 3 glycerol backbone carbons) of from 20 to 25 should comprise greater than or equal to 45 wt %, or greater than or equal to 60 wt %, or greater than or equal to 75 wt %, or greater than or equal to 90 wt %, or greater than or equal to 95 wt %, or greater than or equal to 97 wt %, or greater than or equal to 99 wt %, or greater than or equal to 99.5 wt %, or greater than or equal to 99.9 wt % of the mixed triglyceride blend. These mixed triglyceride blends may also be used as plasticizers and yield outstanding properties and performance with a variety of polymer resins.

The plasticizers according to the current disclosure may also be used with vinyl chloride-type resins, polyesters, polyurethanes, ethylene-vinyl acetate copolymer, rubbers, acrylics, polymer blends such as of polyvinyl chloride with an ethylene-vinyl acetate copolymer or polyvinyl chloride with a polyurethane or ethylene-type polymer.

EXAMPLES

General Procedure for Esterification

Into a four necked 1000 mL round bottom flask equipped with an air stirrer, nitrogen inductor, thermometer, Dean-Stark trap and chilled water cooled condenser were added 0.8 mole glycerol, 1.6 mole acid which has n carbons and 1.6 mole acid which has m carbons (n and m could be equal or the same and could be linear or branched). The Dean-Stark trap was filled with the lighter boiling acid to maintain the same molar ratio of acids in the reaction flask. The reaction mixture was heated to 220° C. with air stirring under a nitrogen sweep. The water collected in the Dean-Stark trap was drained frequently. The theoretical weight of water was obtained in about 3 hours at 220° C. indicating 96% conversion. The reaction mixture was heated an additional 10 hours for a total of 13 hours to achieve near or complete conversion to the triglycerides. The unreacted acid is removed from the crude samples by distillation, after which the non-distilling product is typically filtered to remove any precipitated salts and ash, and typically then extracted twice with 50 mL distilled water at room temperature to remove residual salts. Data on specific triglyceride products are given and shown in the following figures and examples. Composition for the triglyceride products is given in the following manner: a mixed triglyceride of acids with X and Y carbon numbers may theoretically contain products with three chains of length X (denoted XXX), three chains of length Y (denoted YYY), and products with mixed distributions (XXY, XYX, XYY, or YXY where the first and third character represent the terminal (primary) glyceride chains and the second character represents the internal (secondary) glyceride chain). The sum of the carbon numbers for the three chains (including the 3 carbonyl carbons and not including the 3 glycerol backbone carbons) ranges from 20 to 25 for the at least 45 wt % of the plasticizer product. Gas chromatography analysis on the products was conducted using a Hewlett-Packard 5890 GC equipped with a HP6890 autosampler, a HP flame-ionization detector, and a J&W Scientific DB-1 30 meter column (0.32 micrometer inner diameter, 1 micron film thickness, 100% dimethylpolysiloxane coating). The initial oven temperature was 60° C.; injector temperature 290° C.; detector temperature 300° C.; the temperature ramp rate from 60 to 300° C. was 10° C./minute with a hold at 300° C. for 14 minutes. The calculated %'s reported for products were obtained from peak area, with an FID detector uncorrected for response factors. Table 5 provides branching characteristics for the OXO acids used in the Examples.

TABLE 5

$^{13}$C NMR Branching Characteristics of Typical OXO Acids.

| OXO Acid | Average Carbon No. | Pendant Methyls[a] | Total Methyls[b] | Pendant Ethyls | % Carbonyls α to Branch |
|---|---|---|---|---|---|
| $C_7$ | 6.88-7.92 | 0.98-1.27 | 1.94-2.48 | 0.16-0.26 | 11.3-16.4 |
| $C_9$ | 9.4 | n/a | n/a | n/a | 12 |

[a]$C_1$ branches.
[b]Includes methyls on all branch lengths and chain end methyls.

Reference Example 1

Pure Glycerol Esterification with OXO-$C_7$ Acid 0.8 mole pure (Aldrich 99.5%) glycerol was esterified with 3.2 mole OXO $C_7$ acid (7 carbons, and linear, branched and mixtures thereof). The product mixture was extracted with sodium carbonate solution (2 times 100 mL of a 3 wt % solution in distilled water) at 75° C. to remove excess acid. Residual water was then removed by distillation at 100° C. and the product was dried over 2 wt % magnesium sulfate. Some unreacted acid and diester remained after washing; these were re-distilled away. Finally, the mother solution was stirred with 1 wt % decolorizing carbon at room temperature for 2 hours and filtered. The remaining material (mother solution) was analyzed by GC (composition: 99.8% triglyceride, 0.15% residual acid, and 0.007% diglyceride).

Illustrative Example 2

Crude Glycerol Esterification with OXO-$C_7$ Acid 0.8 mole crude glycerol (REG) was esterified with 2.64 mole OXO $C_7$ acid (7 carbons, and linear, branched and mixtures thereof). After unreacted acid was distilled away, the mixture was treated twice with decolorizing carbon as described in Example 1. The remaining material (mother solution) was analyzed by GC (composition: 99.9% triglyceride and 0.1% residual acid).

Reference Example 3

2.5 mole pure (Aldrich 99.5%) glycerol was esterified with 5.0 mole 2-methylvaleric acid (6 carbons and branched) and 5.0 mole OXO $C_9$ acid (9 carbons, and linear, branched and mixtures thereof). After unreacted acid was distilled away, the mixture was extracted once with 10 wt % sodium carbonate solution at room temperature, then dried by stirring over 5 wt % magnesium sulfate for 1 hour. This material was subsequently fractionated under vacuum.

The composition of the mother solution (by GC) before fractionation by distillation is shown herebelow. Unfractionated mother solution: 9.3% 666, 33.9% 669/696, 40.8% 699/969, 16.1% 999.

Illustrative Example 4

0.8 mole crude glycerol (REG) was esterified with 1.6 mole 2-methylvaleric acid (6 carbons and branched) and 1.6 mole OXO $C_9$ acid (9 carbons, and linear, branched and mixtures thereof). The mixture was extracted twice with 10 wt % sodium carbonate solution (145 and 150 mL respectively) at room temperature to remove excess acid, washed with 100 mL distilled water to remove residual sodium carbonate, then stirred over 10 wt % magnesium sulfate at room temperature. The filtered material was then stirred twice with 5 wt % Attapulgas Clay for 2 hours (followed by filtration in each case) to remove color. The material still contained a very small amount of acid and diester, most of which were removed by further distillation. The subsequent material (mother solution) was analyzed by GC (composition: 99.92% triglycerides, 0.014% residual acid, and 0.013% diester).

The composition of the mother solution by GC is shown herebelow. Unfractionated mother solution: 6.8% 666, 33.2% 669/696, 42.9% 699/969, 16.9% 999.

This data shows that using pure or crude glycerol (Example 4 versus Example 3), a similar composition was obtained.

Illustrative Example 5

0.6 mole crude glycerol (EIS-739) was esterified with 1.2 mole 2-methylvaleric acid (6 carbons and branched) and 1.2 mole OXO $C_9$ acid (9 carbons, and linear, branched and mixtures thereof). First the ash was filtered from the reaction mixture then unreacted acid was distilled away. The residual liquid still contained some residual acid and diglycerides. These were further distilled away from the mother liquid. The resultant material (mother solution) was analyzed by GC (composition: 97.5% triglycerides and 2.03% unknown species heavier than triglycerides).

The composition of the mother solution by GC is shown herebelow. Unfractionated mother solution: 6.7% 666, 31.7% 669/696, 41.7% 699/969, 18.1% 999.

This data shows that using pure or crude glycerol (Example 5 versus Example 3), a similar composition was obtained.

Reference Example 6

2.0 mole pure (Aldrich 99.5%) glycerol was esterified with 4.0 mole 2-methylvaleric acid (6 carbons and branched) and 4.0 mole 3,5,5-trimethylhexanoic acid (9 carbons and branched). The crude reaction mixture was fractionated by distillation. Aliquots of the distillate cuts were recombined to provide a material for property and plasticization tests with a composition representative of an unfractionated material, which was analyzed by GC (composition: 99.9% triglyceride and 0.1% diglyceride). The composition of the recombined material by GC is shown herebelow.

Recombined material representative of unfractionated mother solution: 9.9% 666, 34.7% 669/696, 43.4% 699/969, 11.9% 999.

Illustrative Example 7

0.2 mole crude glycerol (REG) was esterified with 0.40 mole 2-methylvaleric acid (6 carbons and branched) and 0.40 mole 3,5,5-trimethylhexanoic acid (9 carbons and branched). The reaction mixture was filtered to remove ash, then washed twice with 50 mL distilled water. The reaction mixture was then treated with 5 wt % decolorizing carbon as described in Example 1, filtered, dried over 10 wt % magnesium sulfate for 2 hours, and refiltered. The remaining material (mother solution) was analyzed by GC (composition: 93.4% triglyceride, 3.4% residual acid, 2.2% diglycerides). The composition of the mother solution by GC is shown herebelow.

Unfractionated mother solution: 9.7% 666, 32.7% 669/696, 37.2% 699/969, 13.8% 999.

Illustrative Example 8

0.213 mole crude glycerol (EIS-739) was esterified with 0.4 mole 2-methylvaleric acid (6 carbons and branched) and 0.4 mole 3,5,5-trimethylhexanoic acid (9 carbons and branched). The material was treated using the same purification procedure as that in Example 7. The remaining material (mother solution) was analyzed by GC (composition: 84.41% triglycerides, 1.9% residual acids, 2.9% diglycerides, 1.4% unknowns, and 9.5% unknowns heavier than triglycerides). The composition of the mother solution by GC is shown herebelow.

Unfractionated mother solution: 10.1% 666, 30.8% 669/696, 32.3% 699/969, 11.2% 999.

Illustrative Example 9

General Procedure for the Use of Triglyceride Esters to Plasticize Poly(Vinyl Chloride)

A 4.5 g portion of the ester sample was weighed into an Erlenmeyer flask which had previously been rinsed with uninhibited tetrahydrofuran (THF) to remove dust. A 0.63 g portion of a 70:30 by weight solid mixture of powdered Drapex® 6.8 (Crompton Corp.) and Mark® 4716 (Chemtura USA Corp.) stabilizers was added along with a stirbar. The solids were dissolved in 90 mL uninhibited THF. Oxy Vinyls® 240F PVC (9.0 g) was added in powdered form the contents of the flask were stirred overnight at room temperature until dissolution of the PVC was complete (a PVC solution for preparation of an unplasticized comparative sample was prepared using an identical amount of stabilizer, 100 mL solvent, and 13.5 g PVC). The clear solution was poured evenly into a flat aluminum paint can lid (previously rinsed with inhibitor-free THF to remove dust) of dimensions 7.5" diameter and 0.5" depth. The lid was placed into an oven at 60° C. for 2 hours with a moderate nitrogen purge. The pan was removed from the oven and allowed to cool for a ~5 min period. The resultant clear film was carefully peeled off of the aluminum, flipped over, and placed back evenly into the pan. The pan was then placed in a vacuum oven at 70° C. overnight to remove residual THF. The dry, flexible, almost colorless film was carefully peeled away and exhibited no oiliness or inhomogeneity unless noted in the data Tables. The film was cut into small pieces to be used for preparation of test bars by compression molding (size of pieces was similar to the hole dimensions of the mold plate). The film pieces were stacked into the holes of a multi-hole steel mold plate, pre-heated to 170° C., having hole dimensions 20 mm×12.8 mm×1.8 mm (ASTM D1693-95 dimensions). The mold plate was pressed in a PHI company QL-433-6-M2 model hydraulic press equipped with separate heating and cooling platforms. The upper and lower press plates were covered in Teflon™-coated aluminum foil and the following multistage press procedure was used at 170° C. with no release between stages: (1) 3 minutes with 1-2 ton overpressure; (2) 1 minute at 10 tons; (3)

1 minute at 15 tons; (4) 3 minutes at 30 tons; (5) release and 3 minutes in the cooling stage of the press (7° C.) at 30 tons. A knockout tool was then used to remove the sample bars with minimal flexion. Near-colorless, flexible bars were obtained which, when stored at room temperature, showed no oiliness or exudation several weeks after pressing unless noted in the data Tables. The bars were allowed to age at room temperature for at least 1 week prior to evaluation of phase behavior with Differential Scanning Calorimetry (DSC) and thermophysical properties with Dynamic Mechanical Thermal Analysis (DMTA).

Illustrative Example 10

Differential Scanning Calorimetry (DSC) and Thermogravimetric Analysis (TGA) Property Study of Triglyceride Esters from Pure and Crude Glycerol Thermogravimetric Analysis (TGA) was conducted on the neat esters using a TA Instruments AutoTGA 2950HR instrument (25-600° C., 10° C./min, under 60 cc $N_2$/min flow through furnace and 40 cc $N_2$/min flow through balance; sample size 10-20 mg). Table 6 provides a volatility comparison of the different triglyceride esters showing that comparable materials prepared from pure and crude glycerols have similar properties. Table 7 provides a volatility comparison of plasticized PVC bars prepared in Example 9, also illustrating that comparable materials prepared from pure and crude glycerols have similar properties. Differential Scanning Calorimetry (DSC) was also performed on the neat plasticizers, using a TA Instruments 2920 calorimeter fitted with a liquid $N_2$ cooling accessory. Samples were loaded at room temperature and cooled to about –130° C. at 10° C./min and analyzed on heating to 75° C. at a rate of 10° C./min. Table 6 provides a glass transition ($T_g$) comparison of the different triglyceride esters. $T_g$s given are midpoints of the second heats (unless only one heat cycle was performed, in which case the first heat $T_g$, which is typically in very close agreement, is given). Table 6 illustrates that comparable materials prepared from pure and crude glycerols have similar $T_g$ properties.

TABLE 6

Volatility and Glass Transition Properties of Triglyceride Esters Prepared From Pure and Crude Glycerols.

| Example No. | TGA 1% Wt Loss (° C.) | TGA 5% Wt Loss (° C.) | TGA 10% Wt Loss (° C.) | TGA Wt Loss at 220° C. (%) | DSC $T_g$ (° C.) |
|---|---|---|---|---|---|
| 1 | 164 | 193.7 | 207.9 | 17.3 | −91.8 |
| 2 | 166.1 | 193.8 | 207.8 | 17.6 | −92.2 |
| 3 | 167.4 | 200.7 | 216.7 | 11.5 | −89.9 |
| 4 | 162.1 | 194.4 | 210.2 | 15.1 | −88.6 |
| 5 | 164.0 | 197.0 | 212.8 | 13.4 | −88.1 |
| 6 | 150.0 | 184.6 | 199.7 | 23.8 | −82.7 |
| 7 | 148.4 | 184.7 | 200.0 | 23.5 | −82.6 |
| 8 | 120.6 | 180.8 | 199.4 | 21.5 | −82.7 |

— Data not obtained.

TABLE 7

Volatility Properties of Neat PVC and PVC Sample Bars Plasticized With Triglyceride Esters Prepared From Pure and Crude Glycerols.

| Example No. (Plasticizer Used in Bar) | TGA 1% Wt Loss (° C.) | TGA 5% Wt Loss (° C.) | TGA 10% Wt Loss (° C.) | TGA % Wt Loss at 220° C. |
|---|---|---|---|---|
| None (Neat PVC) | 129.9 | 192.3 | 255.4 | 6.3 |
| 1 | 187.5 | 225.3 | 248.4 | 4.1 |
| 2 | 188.7 | 227.9 | 247.8 | 3.9 |
| 3 | 193.1 | 236.0 | 256.4 | 2.9 |
| 4 | — | — | — | — |
| 5 | — | — | — | — |
| 6* | 188.5 | 233.3 | 251.8 | 3.4 |
| 7* | 188.6 | 233.5 | 253.2 | 3.5 |
| 8* | 187.4 | 231.8 | 251.3 | 3.6 |

— Data not obtained.
*Sample bars and/or films of 6, 7 and 8 were oily.

Illustrative Example 11

Demonstration of Plasticization of PVC with Triglyceride Esters Via Differential Scanning Calorimetry (DSC)

Differential Scanning Calorimetry (DSC) was performed on the compression-molded sample bars prepared in (PVC:plasticizer ratio 2:1) using a TA Instruments 2920 calorimeter fitted with a liquid $N_2$ cooling accessory. Samples were loaded at room temperature and cooled to –90° C. at 10° C./min, and then analyzed on heating at a rate of 10° C./min to 150-170° C. for plasticized PVC bars, and to 100° C. for the comparative neat PVC bar. Small portions of the sample bars (typical sample mass 5-7 mg) were cut for analysis, making only vertical cuts perpendicular to the largest surface of the bar to preserve the upper and lower compression molding "skins"; the pieces were then placed in the DSC pans so that the upper and lower "skin" surfaces contacted the bottom and top of the pan. Table 8 provides the first heat $T_g$ onset, midpoint, and end for neat PVC and the plasticized bars. A lowering and broadening of the glass transition for neat PVC is observed upon addition of the esters, indicating plasticization and extension of the flexible temperature range of use for neat PVC (for aid in calculating the numerical values of these broad transitions, the DSC curve for each plasticized bar was overlaid with the analogous Dynamic Mechanical Thermal Analysis (DMTA) curve, taken and analyzed as described in Example 12, since the DMTA curve provides additional guidance about the proper temperature regions for the onset, midpoint, and end of $T_g$. Due to the weakness and broad nature of the glass transition for the plasticized samples, a fine comparison of $T_g$ onset, midpoint, and end numeric values in Table 8 is not overly useful; what is important is the general and approximately comparative effect of broadening and lowering seen between analogous pure glycerol- and crude glycerol-derived samples).

TABLE 8

Glass Transition Onset, Midpoint, and End for PVC Bars Plasticized With Triglyceride Esters Prepared From Pure and Crude Glycerols.

| Example No. (Plasticizer Used in Bar) | $T_g$ Onset (° C.) | $T_g$ Midpt (° C.) | $T_g$ End (° C.) | $T_m$ Max (° C.) and $\Delta H_f$ (J/g)$^a$ |
|---|---|---|---|---|
| None (Neat PVC) | 44.5 | 46.4 | 48.9 | not calc. |
| 1 | −60.4 | −36.1 | −12.6 | 55.9, 1.03 |
| 2 | — | — | — | — |
| 3 | −10.5 | −6.3 | −5.9 | not calc. |

TABLE 8-continued

Glass Transition Onset, Midpoint, and End for PVC Bars Plasticized
With Triglyceride Esters Prepared From Pure and Crude Glycerols.

| Example No. (Plasticizer Used in Bar) | $T_g$ Onset (° C.) | $T_g$ Midpt (° C.) | $T_g$ End (° C.) | $T_m$ Max (° C.) and $\Delta H_f$ (J/g)$^a$ |
|---|---|---|---|---|
| 4 | — | — | — | — |
| 5 | — | — | — | — |
| 6* | — | — | — | — |
| 7* | −28.4 | −15.3 | −3.5 | 56.8, 0.75 |
| 8* | −23.6 | −12.6 | −3.6 | not calc. |

— Data not obtained.
*Plasticization is clearly evidenced for sample bars of 7 and 8 (although not to the extent as for sample bars 1 and 2), despite oiliness of these bars and/or films.
$^a$Most sample bars showed a weak melting point ($T_m$) from the crystalline portion of PVC. Often this weak transition was not specifically analyzed, but data is given here in instances where it was recorded.

Illustrative Example 12

Demonstration of Plasticization of PVC with Mixed Triglyceride Esters Via Dynamic Mechanical Thermal Analysis (DMTA)

Three-point bend Dynamic Mechanical Thermal Analysis (DMTA) with a TA Instruments DMA Q980 fitted with a liquid $N_2$ cooling accessory and a three-point bend clamp assembly was used to measure the thermo-mechanical performance of neat PVC and the PVC/plasticizer blend sample bars prepared in Example 9. Samples were loaded at room temperature and cooled to −60° C. at a cooling rate of 3° C./min. After equilibration, a dynamic experiment was performed at one frequency using the following conditions: 3° C./min heating rate, 1 Hz frequency, 20 micrometer amplitude, 0.01 pre-load force, force track 120%. Two or three bars of each sample were typically analyzed; numerical data was taken from the bar typically exhibiting the highest room temperature storage modulus (the bar assumed to have the fewest defects). Glass transition onset values were obtained by extrapolation of the tan delta curve from the first deviation from linearity. The DMTA measurement gives storage modulus (elastic response modulus) and loss modulus (viscous response modulus); the ratio of loss to storage moduli at a given temperature is tan delta. The beginning (onset) of the $T_g$ (temperature of brittle-ductile transition) was obtained for each sample by extrapolating a tangent from the steep inflection of the tan delta curve and the first deviation of linearity from the baseline prior to the beginning of the peak. Table 9 provides a number of DMTA parameters for neat PVC and PVC bars plasticized with the triglyceride esters: $T_g$ onset (taken from tan delta); peak of the tan delta curve; storage modulus at 25° C.; and the temperature at which the storage modulus equals 100 MPa (this temperature was chosen to provide an arbitrary measure of the temperature at which the PVC loses a set amount of rigidity; too much loss of rigidity may lead to processing complications for the PVC material.). The flexible use temperature range of the plasticized PVC samples is evaluated as the range between the $T_g$ onset and the temperature at which the storage modulus was 100 MPa. A lowering and broadening of the glass transition for neat PVC is observed upon addition of both the pure glycerol- and crude glycerol-derived esters, indicating plasticization and extension of the flexible temperature range of use for neat PVC. Plasticization (enhanced flexibility) is also demonstrated by lowering of the PVC room temperature storage modulus upon addition of the esters.

Figure 2A:
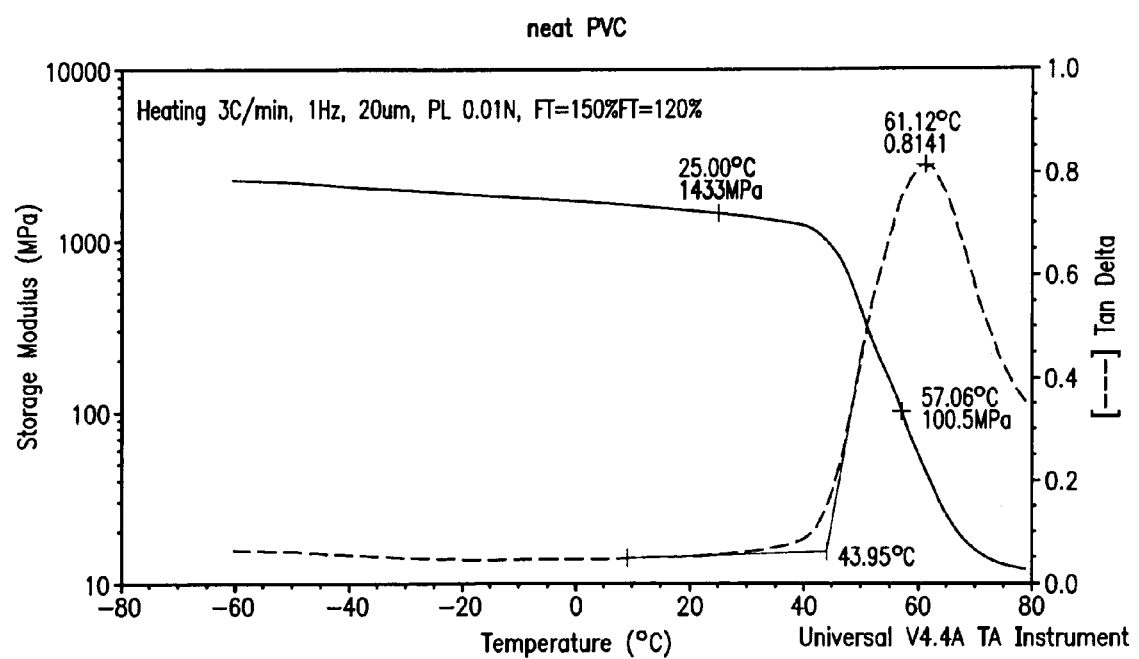
FIG. 2 shows DMTA tan delta and storage modulus curves versus temperature for (a) neat PVC; (b) PVC plasticized with the pure glycerol-derived triglyceride of Example 1; and (c) PVC plasticized with the crude glycerol-derived triglyceride of Example 2.
Figure 2B:
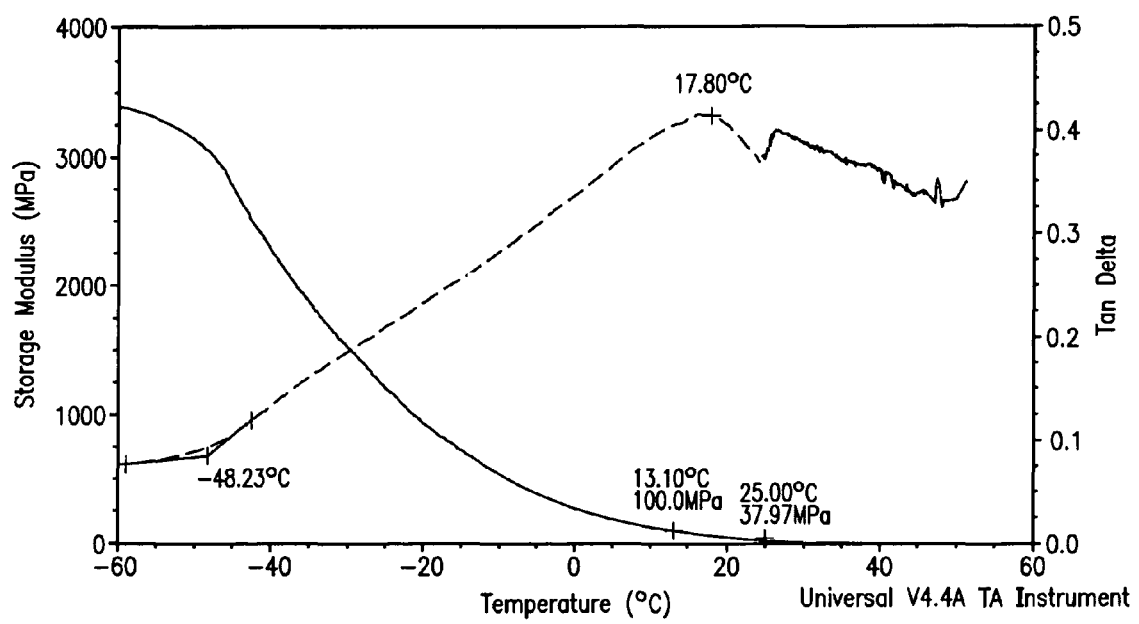
Figure 2C:
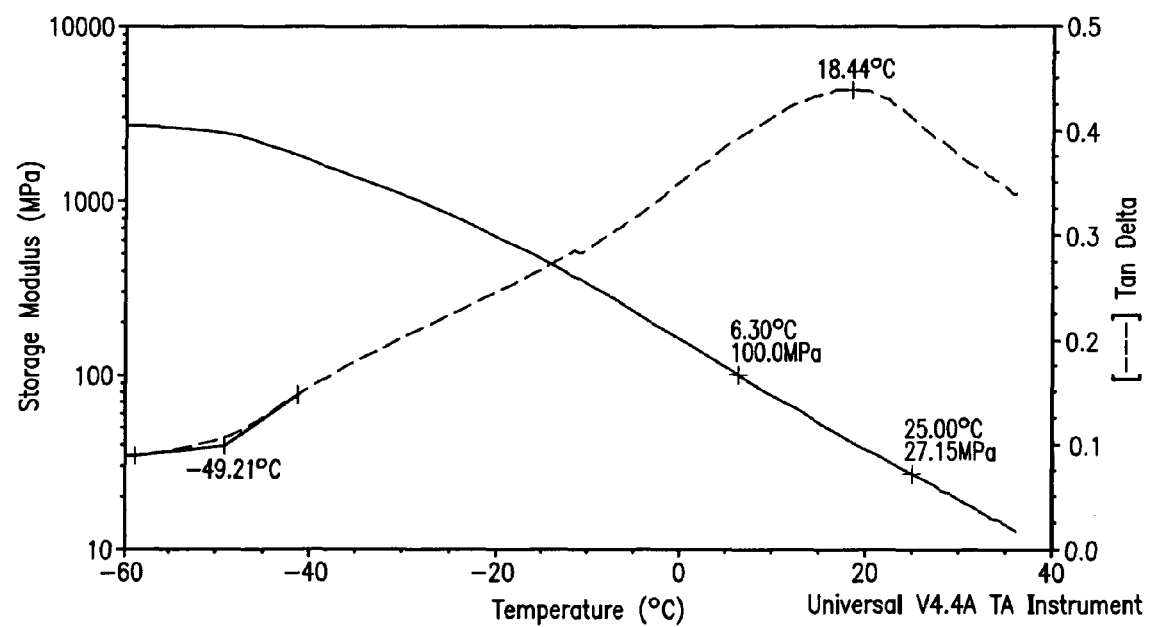

FIG. 2 shows DMTA tan delta and storage modulus curves versus temperature for (a) neat PVC; (b) PVC plasticized with the pure glycerol-derived triglyceride of Example 1; (c) PVC plasticized with the crude glycerol-derived triglyceride of Example 2. Differences in blend performance (shape of the tan delta and storage modulus versus temperature curves) in the low temperature range are likely to be optimizable by adjusting the ratio of PVC to ester in the blend.

TABLE 9

Various DMTA Thermal Parameters for PVC Bars Plasticized
With Triglyceride Esters Prepared From Pure and Crude Glycerols.

| Plasticizer Used in Bar | Tan $\Delta T_g$ Onset (° C.) | Tan $\Delta$ Peak (° C.) | 25° C. Storage Mod. (MPa) | Temp. of 100 MPa Storage Mod. (° C.) | Flexible Use Range (° C.)$^a$ |
|---|---|---|---|---|---|
| None (Neat PVC) | 44.0 | 61.1 | 1433 | 57.1 | 13.1 |
| 1 | −48.2 | 17.8 | 38 | 13.1 | 61.3 |
| 2 | −49.2 | 18.4 | 27.2 | 6.3 | 55.5 |
| 3 | −41.0 | 23.5 | 56.2 | 16.6 | 57.6 |
| 4 | — | — | — | — | — |
| 5 | — | — | — | — | — |
| 6* | −46.8 | 42.7 | 153.1 | 30.3 | 77.1 |
| 7* | −31.6 | 43.8 | 139.8 | 28.8 | 60.4 |
| 8* | −45.3 | 50.1 | 110.8 | 26.6 | 71.9 |

— Data not obtained.
*Plasticization is clearly evidenced for sample bars of 6, 7, and 8 despite oiliness of these bars and/or films.
$^a$Difference between temperature of 100 MPa storage modulus and onset of $T_g$.

Illustrative Example 13

Use of Crude Glycerols for Esterfication

Several crude glycerol samples were received from commercial companies. The composition of these samples are shown in Table 10 below.

TABLE 10

Crude Glycerol Sample Compositions

| Specifications | EIS-739 | EIS-740 | EIS-733 | EIS-724 | EIS 56-81-5 | REG |
|---|---|---|---|---|---|---|
| Glycerol wt % | 65 | 75 | 77 | 82 | 80-88 | 83.7 |
| Methanol wt % | 2.5 | 0.5 | 2 | 0.02 | <1 | 0.04 |
| Water content wt % | 3 | 8 | 4 | 9 | 7-17 | 12 |
| Free fatty acid wt % | n.a | n.a | n.a | n.a | n.a | 0.04 |
| MONG | 22 | 18* | 12 | None | 0-5 | None |
| NaCl | None | n.a | None | 6-8 | 3-5** | 5.6 |
| Ash | 17 | 6. | 8 | 7-8 | n.a | 5.87 |
| pH | 3-5 | 3-9 | 5-8 | | n.a | 5-6 |

MONG: Matter Organic Not Glycerol.
*GC/GCMS shows no MONG.
**Sodium sulfate.

Selected crude glycerols above, along with IRE crude glycerol and a comparative pure glycerol, were esterified using the following representative procedure for REG glycerol: into a three necked 250 mL round bottom flask equipped with an air stirrer, nitrogen inductor, thermometer, Dean-Stark trap and chilled water cooled condenser were added 21.99 g of the crude glycerol (containing 18.40 g (0.2 mole) of actual glycerol), 46.5 g (0.4 mole) 2-methylvaleric acid, and 63.3 g (0.4 mole) 3,5,5-trimethylhexanoic acid. The Dean-Stark trap was filled with 2-methylvaleric acid to maintain the same molar ratio of acids in the reaction flask. The reaction mixture was heated to 220° C. with air stirring under a nitrogen sweep. The water collected in the Dean-Stark trap was drained frequently. The theoretical weight of water was obtained in about 2 hours at 220° C. The reaction mixture was heated an additional 5 hours for a total of 7 hours to achieve complete or near complete conversion to the triglycerides. The procedure used for other glycerols was similar; the amount of total glycerol used was adjusted based on the wt % glycerol in the sample to maintain the same molar amount of actual glycerol.

Figure 3:
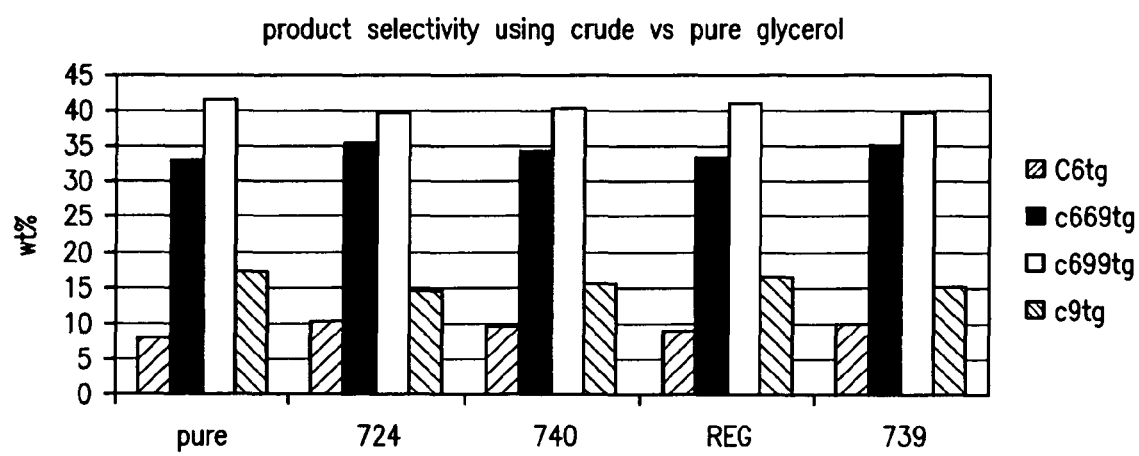
FIG. 3 is a graphical representation of the productivity selectivity of mixed triglycerides produced from pure glycerol and various crude glycerols (C6tg=666 triglyceride; c9tg=999 triglyceride).

The selectivity data for the mixed triglycerides produced as a function of glycerol type is depicted in FIG. 3. FIG. 3 demonstrates that the product selectivity of the mixed triglycerides produced with each of the crude glycerols is comparable to the selectivity of the mixed triglycerides produced with pure glycerol. This surprising result provides for substantial benefits, including, but not limited to, fewer process steps with regard to the use of crude glycerol, process simplification, and less costly input raw materials for the production of triglycerides for plasticizers.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention has been described above with reference to numerous embodiments and specific examples. Many variations will suggest themselves to those skilled in this art in light of the above detailed description. All such obvious variations are within the full intended scope of the appended claims.

What is claimed is:

1. A process for producing a plasticizer comprising:
   (i) recovering an aldehyde/alcohol mixture including at least one linear $C_4$ to $C_{13}$ aldehyde, one branched $C_4$ to $C_{13}$ aldehyde, or a combination thereof and at least one linear $C_4$ to $C_{13}$ alcohol, one branched $C_4$ to $C_{13}$ alcohol, or a combination thereof from a hydroformylation process;
   (ii) oxidizing the aldehyde/alcohol mixture to form a linear, branched or combination thereof $C_4$ to $C_{13}$ acid;
   (iii) esterifying the linear, branched or combination thereof $C_4$ to $C_{13}$ acid with a crude glycerol to yield a linear alkyl triglyceride, a branched alkyl triglyceride, or a combination thereof;
   (iv) removing reacted acid by distillation followed by filtering the esterification product to remove salts and/or ash the followed washing the esterification product with water and/or aqueous carbonate solution to remove salt residuals; and
   (v) purifying the linear, branched or combination thereof alkyl triglyceride to form a plasticizer, wherein the total carbon number of the triester groups ranges from 20 to 25 for greater than or equal to 45 wt % of the plasticizer.

2. The process of claim 1, further including purifying the aldehyde/alcohol mixture of step (i) via distillation before the oxidizing step (ii).

3. The process of claim 1, wherein the at least one branched $C_4$ to $C_{13}$ aldehyde is characterized by a branching of from about 0.8 to about 3.0 branches per molecule.

4. The process of claim 1, wherein the oxidizing step is with oxygen and/or air.

5. The process of claim 1, further including purifying the linear branched or combination thereof $C_4$ to $C_{13}$ acid of step (ii) from the unreacted aldehyde/alcohol mixture via, distillation before the esterfying step (iii).

6. The process of claim 1, further comprising providing a feed for the hydroformylation process from dimerization of a feedstock.

7. The process of claim 6, wherein the feedstock comprises an olefin selected from propylene, butenes, pentenes and mixtures thereof.

8. The process of claim 6, wherein the hydroformylation reaction is catalyzed by a metal selected from Groups 8-10 according to the new notation for the Periodic Table as set forth in Chemical Engineering News, 63(5), 27 (1985).

9. The process of claim 8, wherein the hydroformylation reaction is catalyzed by a metal selected from Rh, Co, and mixtures thereof.

10. The process of claim 9, wherein the hydroformylation reaction is catalyzed by a metal selected from Rh, Co, and mixtures thereof including an organic ligand.

11. The process of claim 1, wherein the total carbon number of the triester groups ranges from 20 to 25 for greater than or equal to 75 wt % of the plasticizer.

12. The process of claim 11, wherein the total carbon number of the triester groups ranges from 20 to 25 for greater than or equal to 95 wt % of the plasticizer.

13. The process of claim 1, wherein the oxidizing step is catalyzed.

14. The process of claim 1, wherein the oxidizing step is not catalyzed.

15. The process of claim 1, wherein the esterifying step is catalyzed by at least one metal selected from Ti, Zr or Sn, or a mixture thereof, or catalyzed by an organic acid.

16. The process of claim 1, further comprising dimerizing a feedstock selected from propylene, butenes, pentenes and mixtures thereof by solid phosphoric acid or a zeolite dimerization to provide a feed for the hydroformylation process.

17. The process of claim 1, wherein the crude glycerol includes from 50 wt % to 95 wt % glycerol.

18. The process of claim 1, wherein the crude glycerol includes from 5 wt % to 50 wt % of methanol, water, fatty acid, Matter Organic Not Glycerol, NaCl, ash, and mixtures thereof.

19. The process of claim 1, wherein the esterifying step further includes from 20 wt % to 80 wt % of a other polyol.

20. The process of claim 19, wherein the other polyol is ethylene glycol, propylene glycol or mixtures thereof.

21. The process of claim 1, wherein the productivity and/or product selectivity of the linear alkyl triglyceride, branched alkyl triglyceride, or combination thereof formed is comparable to that formed when esterifying with pure glycerol.

* * * * *